United States Patent [19]

Kazan et al.

[11] Patent Number: 5,068,437

[45] Date of Patent: Nov. 26, 1991

[54] PROCESS FOR PRODUCING 2-(P-CHLOROPHENOXY) ANILINE

[75] Inventors: John Kazan; James J. Kelly, both of Somerset County, N.J.

[73] Assignee: American Cyanamid Company, Stamford, Conn.

[21] Appl. No.: 65,744

[22] Filed: Jun. 24, 1987

[51] Int. Cl.$^5$ .................................. C07C 209/36
[52] U.S. Cl. .................................. 564/417
[58] Field of Search .......................... 564/417

[56] References Cited

U.S. PATENT DOCUMENTS 3,944,575  3/1976  Villaescusa et al. ............... 260/395

FOREIGN PATENT DOCUMENTS 159447  9/1983  Japan.

Primary Examiner—Glennon H. Hollrah
Assistant Examiner—Peter O'Sullivan
Attorney, Agent, or Firm—H. G. Jackson

[57] ABSTRACT

2-(p-chlorophenoxy)aniline is prepared in a process which provides improved yields and reduction of key impurities. A solution comprising 2-(p-chlorophenoxy)-nitrobenzene, o-dichlorobenzene, and a platinum catalyst is prepared followed by the addition thereto of hydrazine hydrate in water. The temperature is maintained at 80° C. to 110° C. during the addition and until completion of the reaction. The reaction mixture is then cooled to 20° C. to 40° C. and filtration, washing, and distillation workup steps follow.

1 Claim, No Drawings

PROCESS FOR PRODUCING 2-(P-CHLOROPHENOXY) ANILINE

DESCRIPTION OF THE INVENTION

This invention is concerned with an improved process for producing 2-(p-chlorophenoxy)aniline.

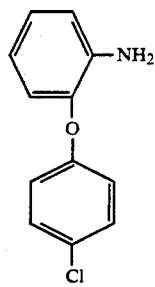

The compound 2-(p-chlorophenoxy)aniline is used in the preparation of commercial central nervous system (CNS) agents, amoxapine

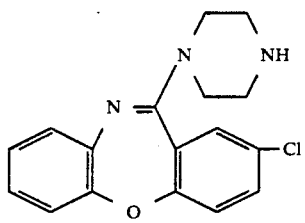

which is disclosed, together with processes for its production, in U.S. Pat. Nos. 3,367,930; 3,444,169; 3,546,226; 3,663,696; and 3,681,357; and loxapine

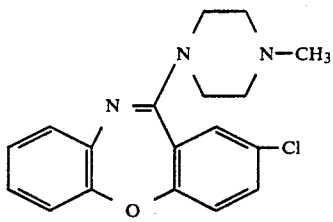

which is disclosed, together with processes for its production, in U.S. Pat. Nos. 3,412,193; 3,444,169 and 3,546,226.

Methods for the preparation of 2-(p-chlorophenoxy)aniline are disclosed in the literature.

One such sequence consists of adding 1,600 to 1,800 parts of iron powder to 5,000 to 5,500 parts of water heated to 35° C. to 50° C. and stirred. Then, while maintaining the temperature below 65° C., 200 to 275 parts of concentrated hydrochloric acid and 2,000 to 2,200 parts of 2-(p-chlorophenoxy)nitrobenzene are added. The mixture is gradually heated with stirring to 95°-115° C. over 0.5 to 2.0 hours and held at this temperature for 8 to 24 hours. The mixture is then cooled to and maintained at 15° C. to 35° C. while sufficient 50% sodium hydroxide is added over 2 to 6 hours to provide a pH of 8.5 to 11.5. Then 6,000 to 6,500 parts of o-dichlorobenzene (ODCB) is added, the mixture heated to 75° C. to 95° C. and stirred for 1 to 3 hours. A filter aid such as Hyflo Super-Cel (75 to 150 parts) is added, this mixture is stirred at 75° C. to 95° C. for 5 to 25 minutes and then clarified. The cake is washed with 1,000 to 15,00 parts of o-dichlorobenzene, the filtrate and wash are combined, stirred and then allowed to separate into two layers at 20° C. to 30° C. The lower organic layer, containing the product is retained and to it is added 75 to 150 or more parts of anhydrous magnesium sulfate, over 20 to 90 minutes with agitation. The mixture is further stirred and then clarified. The filter cake is washed with 700 to 800 parts of o-dichlorobenzene and this wash combined with the filtrate containing 2-(p-chlorophenoxy)aniline which is used in the next step for preparing the aforementioned CNS agents.

We have discovered a process for preparing 2-(p-chlorophenoxy)aniline which provides improved yields, reduction of key impurities and eliminates the handling of the ODCB wet iron waste cake.

In accordance with this new process, 0.1 to 3.0 parts real platinum catalyst such as platinum on carbon (dry or wet) fresh or recycled and 2,000 to 2,200 parts of 2-(p-chlorophenoxy)nitrobenzene are added to 6,000 to 6,500 parts of o-dichlorobenzene. The temperature is adjusted to 80° C. to 110° C. and maintained at that temperature as a solution of 700 to 1,000 parts real hydrazine hydrate in water is slowly added. The temperature is maintained until the reaction is complete (8-24 hours). The mixture is then cooled to 20° C. to 40° C., 0 to 150 parts of a filter aid, such as Hyflo Super-Cel added, the mixture stirred at 20° C. to 40° C. for 5 to 30 minutes and then clarified by filtering. The retained cake from the filtration is washed with 100 to 200 parts o-dichlorobenzene, the filtrate and wash combined, stirred and allowed to separate into two layers at 20° C. to 30° C. The lower organic layer, containing the product, is retained and distilled under reduced pressure at 60° C. to 110° C. until residual water is removed, then cooled to 20° C. to 40° C. If desired the volume may be adjusted with o-dichlorobenzene to the original volume before distillation. The 2-(p-chlorophenoxy)aniline is used in the next step for preparing the aforementioned CNS agents.

What is claimed is:

1. A process for producing 2-(p-chlorophenoxy)aniline which comprises the steps of:
   a) preparing a solution comprising 0.1 to 3.0 parts platinum catalyst, 2,000 to 2,200 parts of 2-(p-chlorophenoxy)nitrobenzene and 6,000 to 6,500 parts of o-dichlorobenzene;
   b) adjusting and maintaining the temperature at 80° C. to 110° C. while adding 700 to 1,000 parts hydrazine hydrate in water with temperature maintainance at 80° C. to 110° C. for 8-24 hours;
   c) cooling to 20° C. to 40° C.;
   d) adding 0-150 parts filter aid;
   e) stirring the mixture for 5 to 30 minutes;
   f) filtering the mixture to clarify the mixture;
   g) washing the filter cake with 100 to 200 parts of o-dichlorobenzene;
   h) combining the filtrate from step f) and the wash from step g);
   i) collecting the lower organic layer, distilling at 60° C. to 110° C.; and then
   j) cooling the 2-(p-chlorophenoxy)aniline product to 20°–40° C.

* * * * *